United States Patent [19]

Beller

[11] 4,171,644

[45] Oct. 23, 1979

[54] MEANS FOR ULTRASONIC TESTING WHEN MATERIAL PROPERTIES VARY

[75] Inventor: Laurence S. Beller, Idaho Falls, Id.

[73] Assignee: The United States of America as represented by the United States Department of Energy, Washington, D.C.

[21] Appl. No.: 882,025

[22] Filed: Feb. 28, 1978

[51] Int. Cl.² ............................................. G01N 29/04
[52] U.S. Cl. .................................................. 73/631
[58] Field of Search ................. 73/602, 625, 627, 628, 73/631

[56] References Cited

U.S. PATENT DOCUMENTS

| 3,690,153 | 9/1972 | Matay | 73/631 |
| 4,004,454 | 1/1977 | Matay | 73/631 X |
| 4,043,181 | 8/1977 | Nigam | 73/631 X |
| 4,068,524 | 1/1978 | Lewis et al. | 73/631 X |

Primary Examiner—James J. Gill
Attorney, Agent, or Firm—Dean E. Carlson; Frank H. Jackson; Paul A. Gottlieb

[57] ABSTRACT

A device is provided for maintaining constant sensitivity in an ultrasonic testing device, despite varying attenuation due to the properties of the material being tested. The device includes a sensor transducer for transmitting and receiving a test signal and a monitor transducer positioned so as to receive ultrasonic energy transmitted through the material to be tested. The received signal of the monitor transducer is utilized in analyzing data obtained from the sensor transducer.

3 Claims, 1 Drawing Figure

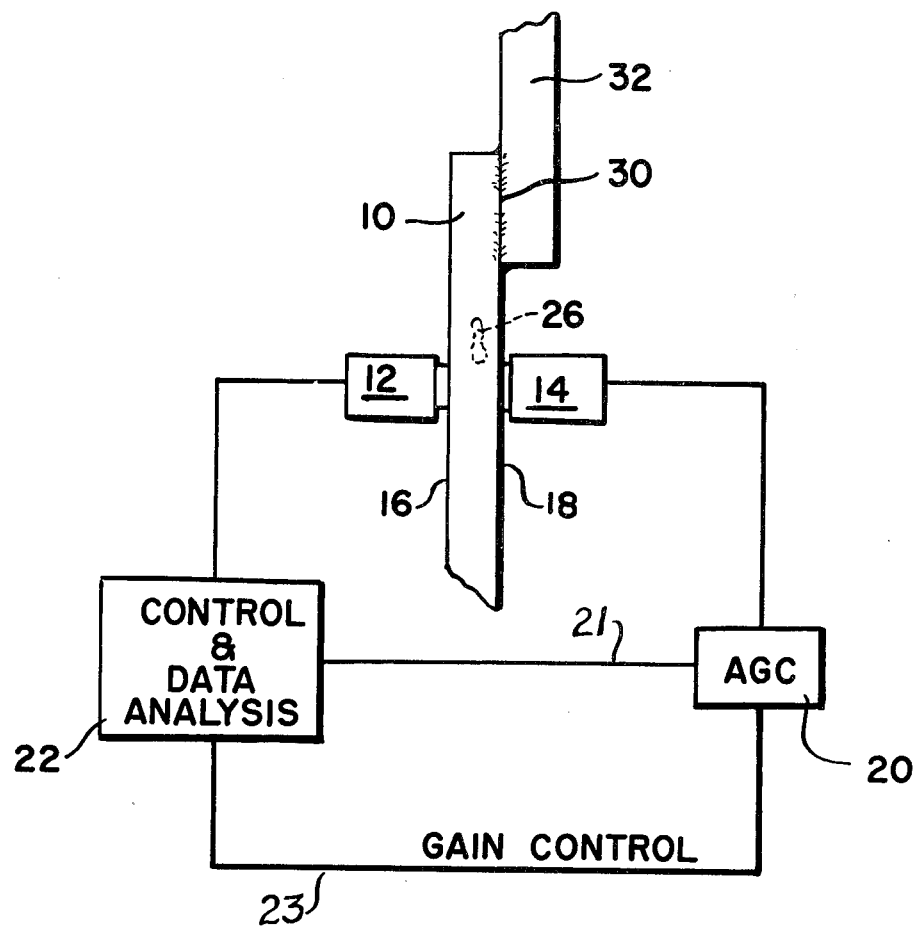

MEANS FOR ULTRASONIC TESTING WHEN MATERIAL PROPERTIES VARY

CONTRACTUAL ORIGIN OF THE INVENTION

The invention described herein was made in the course of, or under, a contract with the U.S. Department of Energy.

BACKGROUND OF THE INVENTION

The crystallographic and metallurgical properties of certain cast and welded engineering materials, such as thick austenitic stainless steels make meaningful nondestructive examination by ultrasonic techniques extremely difficult because of varying attenuation introduced into the ultrasonic beam by the normal properties of the material. The attenuation varies from place to place on the part being examined in a random or unpredictable manner and has the greatest magnitude for ultrasonic examination in the shear-wave mode. The shear-wave mode is often the most useful for detecting important structural discontinuities. The difficulty arises in the fact that the effect of varying sonic attenuation in the material effectively destroys the calibration of the instrument and makes meaningful interpretation of the results difficult, if not impossible.

Standard industrial practice at this time uses handheld transducers and manual interpretation of the instrument reading by a well-trained and highly-skilled ultrasonic technician, who often must correlate many different readings and other data to make a successful examination at each point. The process is time consuming and quite often not meaningful, particularly when examining thick sections. Geometrical constraints often complicate the interpretation. One case of particular significance arises when plates or pipes are joined by welding. The weld zone alone contains the crystallographic and metallurgical complications. The base metal on either side, through which the ultrasonic beam must pass to make the examination, have different values, usually constant, of ultrasonic attenuation.

It is therefore an object of this invention to provide an improved means and method for ultrasonic examination of materials.

Another object in this invention is to provide a method and means for ultrasonic examination of materials where the properties of the normal material result in varying attenuation of the ultrasonic signal as it passes through the material.

SUMMARY OF THE INVENTION

A pulse-echo type ultrasonic testing devive for detecting discontinuities in the material is provided. The device has constant sensitivity despite the presence of varying attenuation introduced into the transmitted ultrasonic beam by the properties of the material. The device includes a search transducer positioned adjacent the material and capable of transmitting an ultrasonic pulse into the material. The search transducer receives the echoes from the material caused by boundaries of the material and any discontinuities therein and transmits these signals to a control means. The monitor transducer is positioned to receive the ultrasound transmitted by the sensor transducer after it passes through the material. The monitor transducer receives the transmitted signal and applies a signal to the control means which will be proportional to the attenuation of the signal after it has passed through the material. This signal from the monitor transducer is used to determine a feedback control, which may have any appropriate mathematical relation to the measured attenuation, for analyzing the data obtained from the received pulse by the search transducer. Correlation of these two signals can be utilized to indicate the presence of any discontinuity and for analyzing the discontinuity to maintain a constant sensitivity for the testing device.

BRIEF DESCRIPTION OF THE DRAWING

The drawing is a block diagram of an apparatus for ultrasonic testing of a material.

DETAILED DESCRIPTION OF THE PREFERRED EMBODIMENT

Referring to the drawing there is shown a device for examination of a test piece 10 by ultrasonic means. Two ultrasonic transducers are utilized. A search transducer 12 is positioned on one side of the workpiece 10 in contact therewith. A monitor transducer 14 is positioned so as to receive the ultrasonic signal from the search transducer, after the ultrasound has passed through the workpiece 10, either by through-transmission, as shown, or by reflection from the side opposite the search transducer 12.

The search transducer acts as a transmitter-receiver operating in the conventional pulse-echo mode. The search transducer 12 transmits an ultrasonic pulse or beam into piece 10 and then receives reflections therefrom. Normally these reflections are from particular boundaries of the piece such as its sides 16 and 18. However, if imperfections are present in piece 10, the normal reflected signal will be altered in attenuation and in the number of received echoes since the imperfection will also reflect a portion of the transmitted ultrasonic beam. For certain materials the amplitude of each echo of a normal signal from a piece 10 without imperfections will vary along the piece due to varying attenuation of an ultrasonic signal caused by the physical properties of the piece. Attenuation will vary from place to place on piece 10 in an unpredictable manner making separation of each echo from the background difficult.

In the embodiment shown, the monitor transducer is positioned to intercept the center of the ultrasonic beam transmitted by search transducer 12 after the beam has passed through piece 10. This centering may be done by either physically coupling the two transducers rigidly to the same manipulating apparatus so they are always in constant aligned relationship with each other or by moving the monitor transducer while holding the sensor transducer stationary. When monitor transducer 14 is picking up the maximum signal from the sensor transducer 12, it can be said to be centered in the beam transmitted by the sensor transducer. The monitor transducer 14 is operated as a receiver only. The strength of the ultrasonic signal received by monitor transducer 14 will be a direct measure of the attenuation of the beam by the piece 10 at the particular location being examined. The signal received by the monitor transducer 14 can therefore be used as a calibration standard for the signal received by the search transducer 12.

The signal received by monitor transducer 14 may be used in the following manner. The received signal or any appropriate mathematical function of the received signal is applied to an automatic gain control amplifier (AGC) 20. An AGC is an amplifier whose output varies according to the variance of an applied signal. Thus, the output of AGC 20 will vary according to the signal received by monitor transducer 14.

AGC 20 and search transducer 12 are coupled to a control and data analysis device 22. Control 22, which may be either a digital or analog device, compares the transmitted signal of monitor transducer 14 with the signal received during prior calibration. The signal from AGC 20 which, in effect, is the signal received by monitor transducer 14 is applied to control 22 by lead 21 and may be subtracted from either the level of the signal transmitted by search transducer 12 or the level of the signal received by monitor transducer 14 or modified as may be required by control 22 in order to ensure constant sensitivity. In normal operation the data analysis device 22 will monitor the difference between the received signal and the received signal obtained during a prior calibration to look for a variation from a normal signal, to look for the presence of additional reflections to those to be expected from the sides of the workpiece 16 and 18 and to look for the time difference between echoes. The combined action of control 22 and AGC 20 ensures constant sensitivity since any attenuation introduced by the workpiece itself, although the workpiece might be normal, will be compensated for by the initial calibration. This becomes an automatic feedback loop, with signal amplitude correction in the search transducer channel based on the received signal in the monitor transducer channel. In performing an examination of a workpiece 10, the two transducers 12 and 14 are moved by either manually or automatic means, in unison so that monitor transducer 14 intercepts and measures the strength of the beam from the search transducer 12, after it has passed through the region of interest in the part being examined. A system for implementing the disclosed scheme for ultrasonic testing, and in particular control 22, is more particularly shown in U.S. Pat. No. 3,857,052, issued Dec. 24, 1974. To the extent this patent contains material necessary for this disclosure, such material is specifically incorporated by reference hereto.

Instability in the circuit just described can arise in the presence of a discontinuity such as defect 26 in piece 10. Defect 26 intercepts some fraction of the transmitted ultrasonic energy, deflecting it out of the transmitted beam, before the beam reaches monitor transducer 14. The resulting drop in signal at the monitor transducer 14 would be incorrectly interpreted as an increase in the attenuation by control 22, causing the sensitivity to be increased, and in many cases causing saturation of the system. This can be compensated for by having the control and data analysis device 22 monitor the received signal of the search transducer 12 for the presence of an echo indicating the presence of a discontinuity. That is, in addition to received echoes from boundaries 16 and 18 there also will be echoes received by transducer 12 from discontinuity 26. If such an echo is present at the same time as a predetermined level of change in the value of the signal received at the monitor transducer 14, then the presence of the discontinuity is deemed confirmed. The output of AGC 20 can then be modified so that constant sensitivity is maintained while the discontinuity may be scanned to determine its size and other features.

The modification of the output of AGC 20 can be based upon a comparison of the signal received by a monitor transducer 14 and the signal received by search transducer 12 to determine the fraction of the transmitted beam intercepted by discontinuity 26. From this an acceptable average feedback level can be determined for AGC 20. The gain of AGC 20 can then be controlled by control means 22 via lead 23 to set the gain of AGC 20 at the desired level.

Alternately, a constant feedback may be maintained by AGC 20 when a discontinuity is present, by corrections made in the means of analyzing the data obtained from the two transducers. Also, the area of discontinuity can be reexamined with a different value of transmitted signal which will automatically vary the value of the signal from AGC 20 since the signal from the monitor transducer 14 will correspondingly be varied.

In examining areas where variation and attenuation due to the piece being examined is confined to subregions of the region of interest, or where the region of interest contains two or more subregions with distinctly different ultrasonic properties, further corrections need to be made. For example, such would arise during the examination of thick pipe welds or examining sandwich structures such as the welding of two pieces as shown at point 30. There piece 32 is welded to piece 10 and the weld is to be examined ultrasonically. The signal received by search transducer 12 is analyzed sequentially as a function of time, which corresponds to the depth of penetration of the beam, for the presence and/or amplitude of echoes. The output of AGC 20 is varied with time by control device 22 to a value appropriate to each region being evaluated when the evaluation reaches the boundary of each region. Therefore, in the examination of the weld at point 30 there would be a first gain for AGC 20 associated with piece 10, a second gain associated with the region of the weld and another gain associated with piece 32. The gain may also be any appropriate mathematical function of position within any or all of the subregions. In the case of a Butt weld, the changes in attenuation as measured by the monitor transducer 14 may often be assumed to lie in the weld zone, with constant attenuation in the parent metal on either side of the weld zone.

The device for monitoring the search transducer signal for the presence of ultrasonic indications and for correcting the search transducer signal with the signal from the monitor transducer, for performing geometric determination of subregions, such as in welded areas, and for controlling gain of AGC 20 may be a digital computer operated as a control and monitoring device in real time, as the examination progresses. A computer may monitor the monitor transducer signal and determine the correct feedback signal to maintain constant sensitivity, monitor the signal for the presence of an ultrasonic indication of a discontinuity, and determine the optimum course of action when an ultrasonic discontinuity is found. With the knowledge of the present position of the search transducer and monitor transducer and a geometrical description of the subregions and their ultrasonic properties, a computer may calculate the parameters for correct evaluation of the search transducer signal as a function of position within the part being examined. Thus, the computer can be programmed to know exactly where a weld will be present and be programmed to include an automatic correction for the output received from AGC 20 according to well known equations for describing the attenuation characteristics of the weld zone area. Alternately, the transducers can be utilized to detect the boundaries of the weld zone by determining the intersection of the areas from the reflected signals received by the search transducer. Analog electrical devices can also be utilized for control 22.

In some situations of practical importance the geometry of the workpiece or its environs is such that a monitor transducer cannot be properly incorporated in the device. The function of the monitor transducer, that of measuring attenuation of the workpiece, can then often be approximated adequately, either by measurements made by auxiliary means, from theory, or from previous experience. This information may then be programmed into the control device or computer such that the whole apparatus functions in a manner to that described, without the aid of the monitor transducer.

The embodiments of the invention in which an exclusive property or privilege is claimed are defined as follows:

1. In a pulse-echo type ultrasonic testing device for detecting discontinuities in a material, an apparatus for maintaining constant sensitivity despite the presence of varying attenuations introduced into the transmitted ultrasonic beam by the properties of the material, comprising:
   a search transducer being positioned adjacent the material and being capable of transmitting an ultrasonic pulse into the material and receiving echoes from the material;
   a monitor transducer being positioned relative to said transducer to receive said pulse after said pulse passes through the material, said monitor transducer being responsive to said received pulse to develop a feedback signal representative of the intensity thereof;
   an automatic gain control amplifier coupled to said monitor transducer and being responsive to said feedback signal to develop a gain signal proportional thereto; and
   a digital computer coupled to said transducers and said amplifier for comparing said transmitted pulse to said received echoes and thereby indicating discontinuities in response to particular attenuation and echoes in said received echoes, and being responsive to said gain signal to continuously vary said comparison according to the value of said gain signal, the gain of said amplifier being controlled by said computer, said computer being programmed to vary the gain of said amplifier in a predetermined manner.

2. The device of claim 1 wherein said digital computer is programmed to vary the gain of said amplifier according to the geometry of particular subregions of the material through which said pulse is propagated.

3. The device of claim 2 wherein said computer is responsive to the coincidence of a predetermined change in value of said gain signal and an echo in said signal received by said search transducer to indicate the presence of a discontinuity.

* * * * *